United States Patent [19]

Neri et al.

[11] 4,405,505

[45] Sep. 20, 1983

[54] CATALYST FOR THE PREPARATION OF PHTHALIC ANHYDRIDE

[75] Inventors: Amleto Neri, Bergamo; Lorenzo Capitanio, Mozzo; Giancarlo Stefani, Gorle, all of Italy

[73] Assignee: Alusuisse Italia S.p.A., Milan, Italy

[21] Appl. No.: 247,357

[22] Filed: Mar. 25, 1981

[30] Foreign Application Priority Data

Apr. 2, 1980 [IT] Italy ................................ 21134 A/80

[51] Int. Cl.³ ........................ B01J 21/06; B01J 23/22; B01J 35/02
[52] U.S. Cl. ................................ 252/461; 252/477 R; 549/248
[58] Field of Search .......................... 252/461, 477 R; 260/346.4

[56] References Cited

U.S. PATENT DOCUMENTS

| 3,674,680 | 7/1972 | Hoekstra et al. | 252/477 R |
| 3,799,886 | 3/1974 | Felice et al. | 252/461 |
| 4,010,238 | 3/1977 | Shiraishi et al. | 252/461 X |
| 4,036,783 | 7/1977 | Blechschmitt et al. | 252/461 |

FOREIGN PATENT DOCUMENTS 1547338  6/1979  United Kingdom .

*Primary Examiner*—W. J. Shine
*Attorney, Agent, or Firm*—Karl F. Ross

[57] ABSTRACT

A catalyst for the preparation of phthalic anhydride is disclosed which comprises a carrier having an open arcuate configuration, e.g. in the form of half rings, and an active portion including $V_2O_5$ and porous $TiO_2$ with the pores having mostly a radius in the 500 to 1,500 Å range.

3 Claims, No Drawings

CATALYST FOR THE PREPARATION OF PHTHALIC ANHYDRIDE

FIELD OF THE INVENTION

This invention relates to the preparation of phthalic anhydride by oxidation of o-xylol or naphthalene, and in particular, to a catalyst for use in the preparation of phthalic anhydride.

BACKGROUND OF THE INVENTION

In conventional processes for preparing phthalic anhydride by oxidation of ortho-xylol or naphthalene in the vapor phase with an oxygen-containing gas, supported catalysts are employed. Such catalysts usually comprise, as the active portion, vanadium pentoxide and titanium dioxide, with minor additives such as stabilizers, promoters, etc., and as the support or carrier, particles of a non-reactive material, such as silicates or alumina, which supply the surface area, strength and stability required for the catalyst.

The catalysts for phthalic anhydride used in the past comprised supports or carriers preferably in the forms of balls, saddles, or cylinders.

For the active portion of the catalysts for phthalic anhydride, it has been common practice to use titanium dioxide with pores so distributed as to have pore diameters mostly in the 0.10 to 0.50 microns range.

While such known catalysts exhibit satisfactory catalytic activity in the preparation of phthalic anhydride, they are not entirely devoid of shortcomings, as connected with their potency and selectivity levels.

OBJECTS OF THE INVENTION

It is a principal object of the present invention to provide a catalyst for use in the preparation of phthalic anhydride, which has improved properties over conventional catalysts as relates to its performances and in particular its potentiality and selectivity.

It is another object of the present invention, to provide a catalyst which has a higher activity or durability (life).

DESCRIPTION OF THE INVENTION

According to one aspect of the present invention, there is provided a catalyst for the preparation of phthalic anhydride by oxidation of ortho-xylol or naphthalene, comprising an active portion distributed over an inert support or carrier, characterized in that the inert support or carrier comprises elements having an open arcuate configuration.

The detailed description which follows will serve to make the structure and advantages of the catalyst according to this invention more clearly understood.

In the description, the expression "potency of the catalyst" refers to the amount of raw material which can be converted by contacting the catalyst per unit volume of catalyst in the reactor.

Thus, the catalyst for the preparation of phthalic anhydride comprises, in accordance with this invention, a support or carrier made up of open arcuate shape particles. The arc defined by the support particle may be an arc of a circle, or of an ellipse, or parabola, etc., the arc may have portions of different radius. Preferably, the arc defined by the support particles is an arc of a circle, and the preferred support particles are in the form of half rings, although other forms may be utilized in the present invention. Accordingly, in the following description, specific reference will be made to the half ring form of the support, without the possible configurations for the catalyst support being limited to such form.

Preferably, rings are utilized whose outside diameters range from 6 to 13 mm, inside diameters from 4 to 8 mm, and heights from 4 to 8 mm. By way of example, a preferred configuration of half ring has, in accordance with this invention, an outside diameter of 9 mm, an inside diameter of 6 mm, and a length of 6 mm.

The half ring support of the catalyst of this invention has a geometric specific surface area (geometric surface area per reactor unit volume) which is higher than that of conventional supports or carriers for oxidizing ortho-xylol or naphthalene to phthalic anhydride, affording a considerable improvement of the catalyst overall performance. In Table 1 herein below, comparative data are given for the geometric surface areas provided by catalyst supports in the form of balls of various diameters, cylinders, and half ring supports according to the invention.

TABLE 1

| Support (all dimensions in mm) | Total geometrical surface area in the tube+ (square meters) |
| --- | --- |
| Balls, Dia. = 6 | .80 |
| Balls, Dia. = 8 | .54 |
| Saddles, 8 × 8 | .77 |
| Rings, 8 × 5 × 6 | .85 |
| Half rings, 9 × 6 × 6* | 1.05 |

+Dia. = 25 mm; h = 290 cm.
*For rings and half rings, the three dimensions relate respectively to the outside diameter, inside diameter, and length.

This increased geometric surface area affords higher potentiality, selectivity, and durability or activity of the catalyst, with all other performances being equivalent, with respect to the cited conventional catalysts or supports.

Thus, for the same selectivity, it becomes possible to achieve a higher potency, in that one can have a larger amount of active mass in the reactor, correspondingly to the increased surface area of the support, without increasing the thickness or depth of the catalytic layer. Thus, a higher flow rate of reactant to be treated (e.g. ortho-xylol) can be achieved for a given thickness of the catalytic layer in the reactor. Table 2 herein below, illustrates in fact a comparison of the potencies of conventional catalysts using known supports, and of a catalyst according to this invention, said potentiality being expressed in terms of ortho-xylol mass flow rate versus the same given thickness or depth of the catalytic layer.

TABLE 2

| Support (all dimensions in mm) | Total geometrical surface area in the tube (m²) | O—xylol mass flow rate (g/hour) |
| --- | --- | --- |
| Balls, Dia. = 6 | .80 | 230 |
| Balls, Dia. = 8 | .54 | 156 |
| Saddles, 8 × 8 | .77 | 221 |
| Rings, 8 × 5 × 6 | .85 | 244 |
| Half rings, 9 × 6 × 6 | 1.05 | 302 |

Conversely keeping a supply of starting reactants constant with respect to other conventional supports, with the catalysts according to this invention, it becomes possible to achieve higher selectivities thanks to the possibility of having the same total amount of catalyst active portion in the tube, with a smaller depth (thickness) of the catalytic layer, and accordingly reduced overoxidation phenomena. In fact, it is well known that the depth of the catalytic layer in a reactor must be chosen in the faces of contradictory requisites, in that on one hand, greater depth provides an increased catalytic active mass with attendant increased conversion outputs, while on the other hand excess depth may result in overoxidation phenomena and the production of undesired by-products. Thus, it is of importance that a catalyst should present a larger active mass distributed over a thinner catalytic layer, which is indeed accomplished by the catalyst according to this invention.

Of course, the catalyst of this invention ensures a simultaneous increase of both the potentiality and selectivity of the catalyst with a smaller thickness catalytic layer with respect to conventional supports and a slightly lower feed than shown in Table 2, but still much higher than is afforded by other conventional supports.

The open arcuate shape of the support or carrier according to the invention affords an optimum compaction of the particles in a catalytic bed arranged within a reactor, and a much more uniform distribution of voids in said catalytic bed over that obtainable with catalysts on conventional supports. Thus, the formation of preferential channels through the catalytic bed for the passage of reactants is effectively prevented, and an improved turbulence and consequently improved thermal exchange with the reactants are obtained.

Therefore, the temperature diagram pattern through the catalytic bed according to the invention is, for a given set of conditions, flatter than with conventional catalysts, wherein on account of the less homogeneous distribution of the voids and accordingly of the less intense thermal exchange, there often occur temperature peaks with attendant formation of undesired by-products. Thus, as an example, for a given depth of the catalytic layers, with the catalyst according to this invention one can operate at temperatures below about 370° C., to reach temperature peaks which do not exceed 420° C., whereas with catalysts of conventional configuration (balls, saddles, etc.), one has to operate at temperatures of 400° C., while reaching in the catalytic mass temperature peaks of approximately 460°–470° C., which adversely affects the desired product yield.

By virtue of this flatter temperature pattern, and attendant reduced thermal stress, a longer life or active durability is achieved for the catalyst of this invention with respect to conventional catalysts.

For manufacturing the supports or carriers of the catalysts according to this invention, any inert material may be utilized which is normally used in the manufacture of catalyst supports, such as alumina or steatite (magnesium silicate).

The present invention also relates, according to a further embodiment thereof, to the active mass of the catalyst for the preparation of phthalic anhydride, which can be utilized in conjunction with the catalytic support or carrier provided by the invention. The active portion of the catalyst comprises, preferably, a mixture of vanadium pentoxide ($V_2O_5$) and titanium dioxide ($TiO_2$), preferably in a ratio by weight of 1:5 to 1:20, e.g. of 1:13. Advantageously, titanium dioxide in the anatase form is used. This remains stable during the reaction resulting in phthalic anhydride formation without undergoing substantial conversion into the less preferred rutile form, because of the lower operating temperatures which can be used with the inventive catalyst as a result of the particular configuration of the support, as explained hereinabove.

Advantageously, in the catalyst according to the invention, titanium dioxide is used with a porosity distribution such that smaller size pores are used than is generally required with conventional catalysts. It is preferred in this respect to use titanium dioxide having more than 50%, preferably more than 80%, of the pore volume with radii in the 500 to 1,500 Ångstrom range. It has been found that such a pore structure is effective to further increase the selectivity of the catalyst for the formation of phthalic anhydride.

In addition to the vanadium pentoxide and titanium dioxide components, the catalyst according to this invention may also contain minor amounts of other components which can improve its performances, such as potassium, which imparts a particular stability to the catalytic system, or molybdenum, which stabilizes the anatase form of titanium dioxide.

The advantages to be secured with catalysts according to this invention are illustrated by the following examples, which are given herein by way of illustration and not of limitation of the invention true scope.

In the examples here below, the performance of the catalysts are reported after completion of the setting period, since phthalic anhydride catalysts are known to require a setting time of at least one month before they can produce their best performance.

The tests were run over a period of about 6 months, whereafter the catalyst was discharged and subjected to analysis to determine the percentage of the rutile form of $TiO_2$, which constitutes an indication of the degree of ageing undergone by the catalyst.

EXAMPLE 1

Preparation of the Catalyst

In a titanium pan mounted on a gear motor turning at 15 rpm and having its axis set at a 45° angle to the base, 2,000 g of half ring carrier or support (9×6×6, O.D.×I.D.×length) are loaded.

The charge is refined in a colloidal mill with 1,300 ml water, 297 g anatase having a total pore volume of 0.504 cm$^3$/g, 80% whereof is made up of pores having a radius in the 500 to 1,500 Å range; to this suspension, 240 g of thiourea are added, and the mixture is further refined in the colloidal mill; 155 ml of a vanadyl oxalate solution are then added which contains 14.7 g $V_2O_5$ per 100 ml solution and 1.37 g KCl are also added.

The active component suspension is then poured into a 3,000 ml beaker equipped with a stirrer and fed by means of a metering pump of the membrane type, drop by drop, over the support or carrier, as heated to 210° C., at a rate of 450 ml/hour. Upon completion of the dripping step, heating is continued for another hour at 210° C.

Catalyst yield: 2,316 g.

Percent of final active portion on the support or carrier: 15.8% by weight.

The catalyst, as prepared in the aforementioned manner, is loaded into a reactor comprising a 25 mm I.D. tube submerged in a molten salt bath and provided on its inside with a sleeve having a 3 mm diameter for a movable thermocouple for hot spot control; 1,040 g of catalyst were been loaded, This is calcined by passing 500 Nl/hour of air through the catalyst, as pre-heated by the molten salts to a temperature of 300° C.; the treatment is continued raising the temperature by 10° C. every hour until 390° C. are reached (total duration, 9 hours).

The maximum rate of supply of the air/hydrocarbon mixture (4,640 Nl/hour air and 300 g/hour o-xylol) is attained gradually in about two weeks, complete setting of the catalyst (for best performance) being achieved in approximately one month.

At this point, with the salts at a temperature of 380° C., the yield by weight is 116% if expressed in terms of phthalic anhydride versus 100% fed o-xylol. This yield is maintained unaltered over about six months, whereafter the catalyst is discharged and analyzed: $TiO_2$ comprises entirely rutile-free anatase.

EXAMPLE 1/A, CONTROL

The catalyst is prepared with the same equipment and procedures as in Example 1, using a ring-shaped support or carrier ($8 \times 5 \times 6$, O.D.$\times$I.D.$\times$length).

In a colloidal mill, 241 g anatase $TiO_2$ are refined with 1,100 ml $H_2O$; to this suspension, there are added 195 g thiourea, followed by further refining in the colloidal mill. To this suspension, there are added 129 ml of a vanadyl oxalate solution at 14.7% $V_2O_5$ and 1.11 g KCl. This suspension is dripped with the same procedure as described in Example 1 onto 2,000 g ring support or carrier. Thereafter the process was identical to that of Example 1.

Catalyst yield: 2,256 g.

The percentage of active portion (versus the support) is 12.8%. The depth of the catalytic mass is practically the same as in Example 1.

The resulting catalyst is then loaded and calcined in a pilot system as described in Example 1.

Amount loaded: 1,130 g.

One then operates as in Example 1, with a supply at 300 g/hour o-xylol and 4,640 Nl/hour air. It will be necessary to maintain the salts at 390° C. if one is to obtain good quality phthalic anhydride.

After about one month, the yield in phthalic anhydride versus 100% o-xylol reaches a maximum of 111% by weight. Subsequently, in order to retain the good quality of the product, it has been necessary to further raise the salt temperature, until after six months, 410° C. are reached (in the meantime, the yield dropping to 105%). This is due to the distribution of the voids through the catalytic layer being less homogeneous with a resulting poorer thermal exchange. In the discharged catalyst, the $TiO_2$ rutile content is 20%.

It will be apparent, therefore, that for a given volume of catalyst and feed, with a conventional ring catalyst one must operate at higher temperatures, thereby secondary reactions occur which result in by-products, and decrease the yield in phthalic anhydride.

Moreover, the higher temperatures involved, lead to the formation of rutile, with consequent reduction in the catalyst life and selectivity.

EXAMPLE 1/B, CONTROL

A catalyst is prepared on spherical supports (Dia. 6.5 mm) following a quite similar procedure to Example 1. The active portion percentage has been proportionately reduced in accordance with the bulk density ratio and specific surface area ratio of the two supports or carriers (half rings and balls). The active mass percentage thus calculated is 7% of the support.

1,850 g of this catalyst have been loaded into the same reactor as described hereinabove. It has been observed that it was not possible to operate with the same mass flow rate (300 g/hour) of o-xylol owing to the very poor quality of the resulting phthalic anhydride, even at very high temperatures of the salts. It has been instead possible to operate at 230 g/hour o-xylol and 3,250 Nl/hour air, with a yield (salts at 385° C.) of 114%. With higher percentages of active mass on the same spherical support, the yield has been lower.

EXAMPLE 2

With the catalyst of Example 1, the oxidation of naphthalene with air has been examined.

1,040 g catalyst have been loaded into the same reaction tube as in Example 1.

Onto this catalyst, 220 g/hour naphthalene and 4,400 Nl/hour air at 370° C. are passed. A yield of 104% by weight in phthalic anhydride is obtained based upon the 100% naphthalene supplied.

EXAMPLE 3

A suspension of 297 g anatase $TiO_2$, having a total pore volume of 0.492 $cm^3/g$, 80% whereof comprises pores with radii in the 500 to 1,500 Å range, in 1,300 $cm^3$ water, is added to a vandyl oxalate solution containing an amount of vanadium corresponding to 22.8 g $V_2O_5$.

A solution is added containing 1.37 g KCl and 240 g ammonium sulphocyanide in 1,000 $cm^3$ $H_2O$.

This suspension is used to coat 2,000 g support in half rings ($9 \times 6 \times 6$ mm) form with the same equipment and procedures as described in Example 1.

The amount of final active portion, based upon the support, is 15.9%.

1,040 g of the catalyst thus obtained are loaded into the same reaction tube as in Example 1.

A mixture of 330 g/hour o-xylol and 4,600 Nl/hour air (corresponding to 71.7 g o-xylol per $Nm^3$ air) is then added until standard conditions are gradually achieved. After about one month, stable yields of 114.5% phthalic anhydride based upon the 100% o-xylol supplied are obtained. After six months of operation in these conditions and with constant results, the discharged catalyst is rutile-free.

We claim:

1. A catalyst for the preparation of phthalic anhydride by oxidation of ortho-xylol or naphthalene, comprising as the active component thereof a mixture of vanadium pentoxide and titanium dioxide in a 1:5 to 1:20 ratio by weight, said titanium dioxide having more than 50% of the total pore volume thereof with radii in the 500 to 1,500 Ångstrom range, said active component being distributed over an inert support or carrier comprising half-rings.

2. A catalyst according to claim 1, wherein said support or carrier comprises elements substantially in the form of half rings having an outside diameter in the 6 to 13 mm range, an inside diameter in the 4 to 8 mm range, and a height in the 4 to 8 mm range.

3. A catalyst according to claim 1 or claim 2 wherein said pores having a radius in the 500 to 1,500 Angstrom range account for more than 80% of the total pore volume.

* * * * *